United States Patent [19]

Bragg et al.

[11] Patent Number: 4,749,276
[45] Date of Patent: Jun. 7, 1988

[54] LONG PATH ABSORPTION CELL

[75] Inventors: Susan L. Bragg, Richmond Hts.; Charles E. Wiswall, Hazelwood, both of Mo.

[73] Assignee: McDonnell Douglas Corporation, St. Louis, Mo.

[21] Appl. No.: 821,795

[22] Filed: Jan. 23, 1986

[51] Int. Cl.[4] .................................. G01N 21/09
[52] U.S. Cl. ............................ 356/246; 250/343; 356/440
[58] Field of Search ............... 356/246, 440; 250/343; 350/588; 219/219; 372/107

[56] References Cited

U.S. PATENT DOCUMENTS

| 1,791,254 | 2/1931 | Brockdorff | 350/588 X |
| 3,906,226 | 9/1975 | Okabe et al. | 250/373 X |
| 3,944,834 | 3/1976 | Chuan et al. | 356/243 X |

FOREIGN PATENT DOCUMENTS 3014248 10/1981 Fed. Rep. of Germany ...... 356/246

OTHER PUBLICATIONS

White, J. U., "Long Optical Paths of Large Aperture", J. Opt. Soc. Am., No. 32 (1942), pp. 285–288.
Eng, R. S. et al., "Tunable Diode Laser Measurement of Water Vapor Line Parameters in the 10 to 15 μm Spectral Region", J. of Mol. Spectry., No. 74 (1979), pp. 388–399.
Baumeister, T. et al., Mark's Standard Handbook for Mechanical Engineers, 8th Ed., pp. 6–41.
Watkins, W. R. et al., "Automation of Long Path Absorption Cell Measurements," Rev. Sci. Instrum., No. 50 (1979), pp. 86–92.
Briesmeister, R. A. et al., "Long Path Length Temperature-Controlled Absorption Cell for Spectroscopic Studies of Radioactive Compounds", Applied Spectroscopy, No. 38 (1984), pp. 35–38.

*Primary Examiner*—Davis L. Willis
*Assistant Examiner*—Matthew W. Koren
*Attorney, Agent, or Firm*—Cohn, Powell & Hind

[57] ABSTRACT

A small volume long path absorption cell of the White-type may be used with condensable samples. The absorption cell is temperature controlled and may be operated over a temperature range of −10 degrees C. to 80 degrees C. To prevent condensation of the sample on the mirror surfaces the mirrors are individually temperature controlled and maintained a few degrees above the ambient temperature of the absorption cell. The mirrors are mounted on an Invar framework which is cantilevered from one end of the cell so that variation of the path length due to thermal expansion is minimized. The cell temperature is controlled by a jacket having a heating or cooling fluid. The controls of the mirrors for the cell are adjustable from the exterior of the cell and the entrance paths for the mechanism are sealed so that the cell can be operated at both above and below atmospheric pressure.

19 Claims, 4 Drawing Sheets

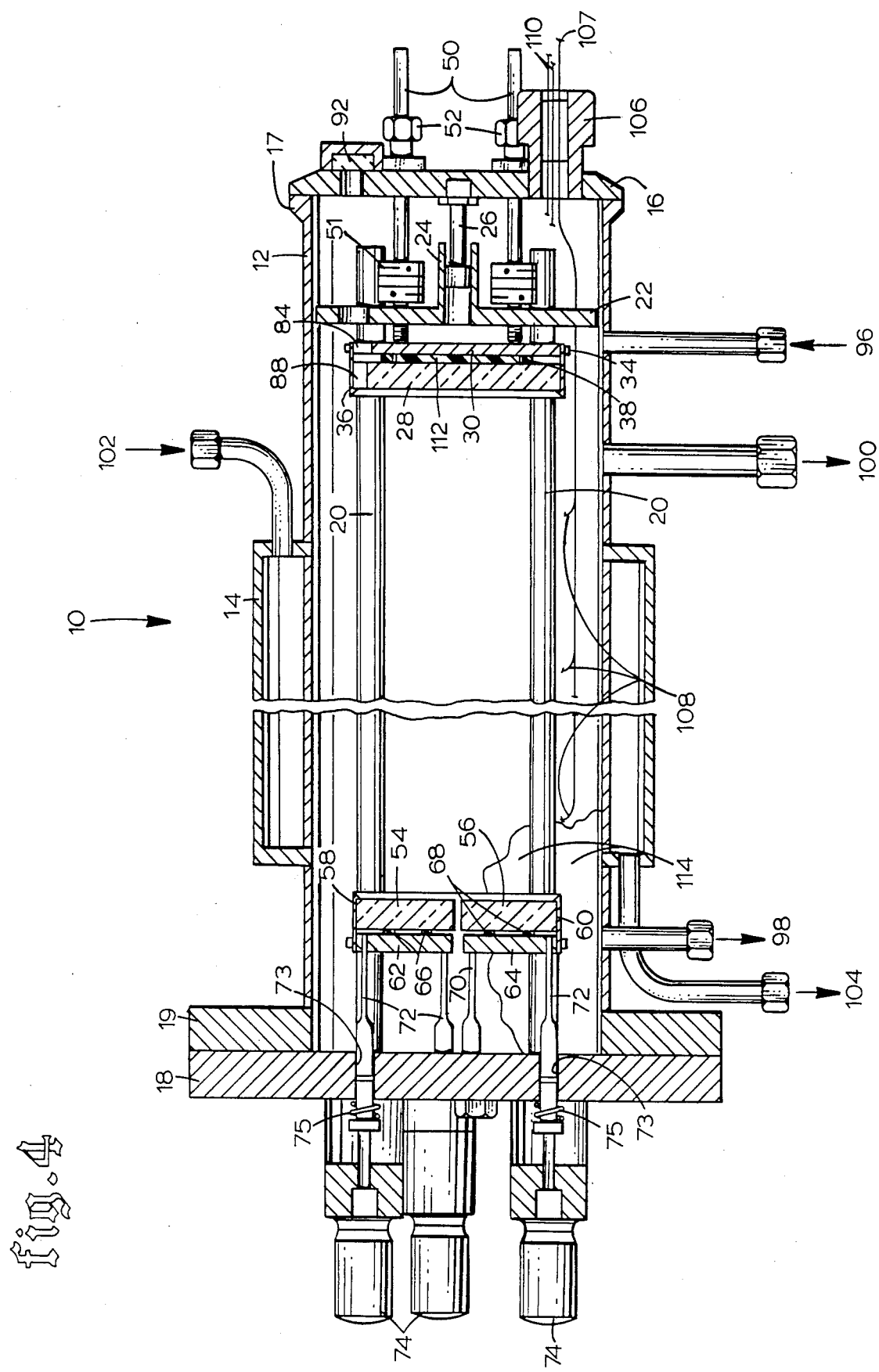

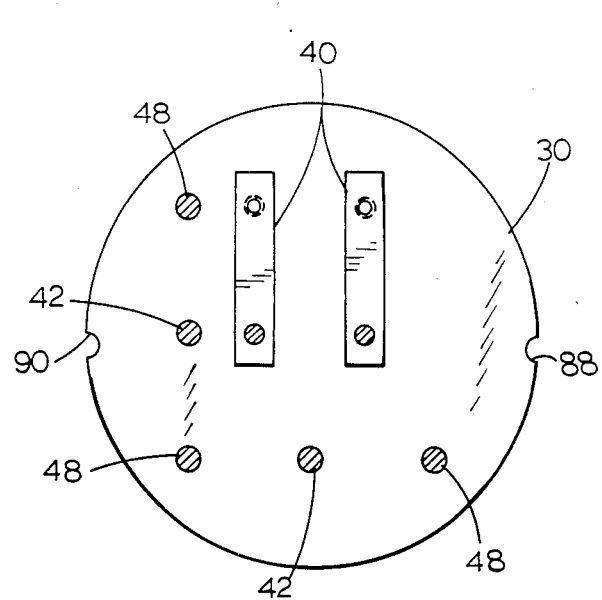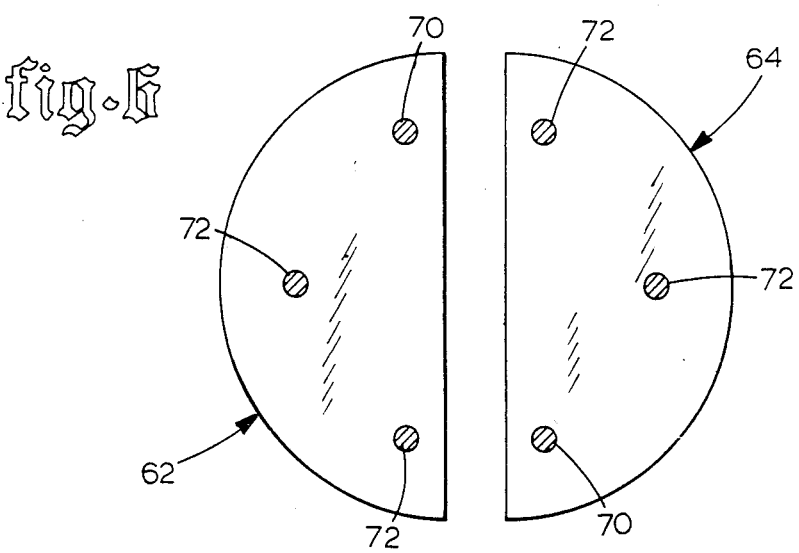

LONG PATH ABSORPTION CELL

BACKGROUND AND SUMMARY OF THE INVENTION

Applicants have produced an improved long path length, temperature controlled, absorption cell designed to measure optical absorption of gas phase samples. Applicants' device is of the type known as a White-type absorption cell. These cells are based on optical configurations proposed by J. U. White in the *J. Opt. Soc. Am.*, Vol. 32, (1942) pp. 285–288. The purpose of White-type absorption cells is to achieve long path lengths using multiple reflections and traversals within a small volume.

Many cells based on this theoretical proposal have been constructed, including a six meter base path length cell constructed by the Jet Propulsion Laboratory and located at the National Solar Observatory at Kitt Peak, Az. A White-type cell is commercially available from Laser Analytics Division of Spectra-Physics, Inc. In addition, a number of different designs have been recorded in the literature including W. R. Watkins and R. G. Dixon *Rev. Sci. Instrum.*, Vol. 50, (1979), pp. 86–92; R. A. Briesmeister, G. W. Read, K. C. Kim and J. R. Fitzpatrick, *Applied Spectroscopy*, Vol. 38, (1984), pp. 35–38 and R. S. Eng and A. W. Mantz, *J. of Mol. Spectry.*, Vol. 74, (1979), pp. 388–399. The disclosures of these publications are incorporated by reference herein.

Applicants' White-type cell permits very small absorption coefficients to be measured in condensable gases over a wide range of temperatures. Applicants' device has a long optical path and the cell maintains its stability over a wide range of temperatures and path lengths. Applicants' device has the mirror adjusting controls accessible on the exterior of the cell. The mirror spacing in applicants' device is stabilized so that the path length is constant over a very wide range of temperatures. Applicants' cell is useable over a wide range of temperatures, even with gas samples containing condensable fractions. Applicants' mirror surfaces are heated to prevent condensation of the sample on the mirror surfaces during use. Applicants also control the temperature of the entire absorption cell to permit elevated pressure (and high densities) of condensable samples to be used. In addition, applicants structure is incorporated within a small volume which permits much smaller samples of gas to be used, permitting use of a smaller and more homogeneous gas sample, thus increasing the accuracy of the measurements obtained.

The intensity of the light observed from a White-type cell following absorption by a gas sample depends upon the following equation: $\ln(I/I_0) = -\sigma_D n L$ where $\ln$ = the natural logarithm, $I$ = the observed light intensity, $I_0$ = the initial light intensity, $\sigma_D$ = the absorption cross section constant of the gas sample; $n$ = the pressure and $L$ = the path length. Applicants' device permits the pressure and/or the path length to be increased thus permitting increased accuracy in the measurements taken for any given gas, such as the value of $\sigma_D$.

Applicants' device can be used in connection with a spectrophotometer to measure the composition of an unknown gas, for example, flue gases or stack gases, or to test the atmosphere for trace impurities and pollutants. The device can also be used to measure the fundamental properties of gases and gas mixtures of known composition. For example, to measure $\sigma_D$ by measuring the absorption of light in a gas sample of known composition as a function of the wavelength of light used.

It is thus an object of applicants' invention to produce a compact White-type cell capable of taking measurements of small, homogeneous gas samples.

It is a further object of applicants' invention to produce a White-type absorption cell in which the path length is stabilized over a wide range of operating temperatures.

It is a further object of applicants' invention to provide a White-type cell having a design which permits very small absorption coefficients to be measured in condensable gases.

It is an object of applicants' invention to produce a White-type cell which can function to measure condensable gases at elevated pressure.

It is an object of applicants' invention to provide a White-type cell having heated mirror surfaces to prevent condensation of gases on the mirror surfaces.

It is an object of applicants' invention to provide a White-type cell in which all mirror adjustment and controls are accessible from the exterior of the cell, permitting fine adjustment in use.

It is an object of applicants' invention to stabilize the mirrors and optical path on an Invar framework.

It is an object of applicants' invention to provide a temperature control for a White-type absorption cell and to provide means of controlling the temperature of the absorption cell during use.

It is a further object of applicants' invention to provide a White-type cell which can operate to measure corrosive gases and compositions.

Further objects and advantages of applicants' device will be apparent from the following description of the drawings and description of the preferred embodiments.

BRIEF DESCRIPTION OF THE DRAWINGS

FIG. 4 is a broken cross sectional view of applicants' cell;

FIG. 6 is a schematic view of the adjustment layout of the Dee mirrors; and,

FIG. 7 is a schematic view of the adjustment details of the Tee mirror.

DESCRIPTION OF THE PREFERRED EMBODIMENTS

Figure 1:
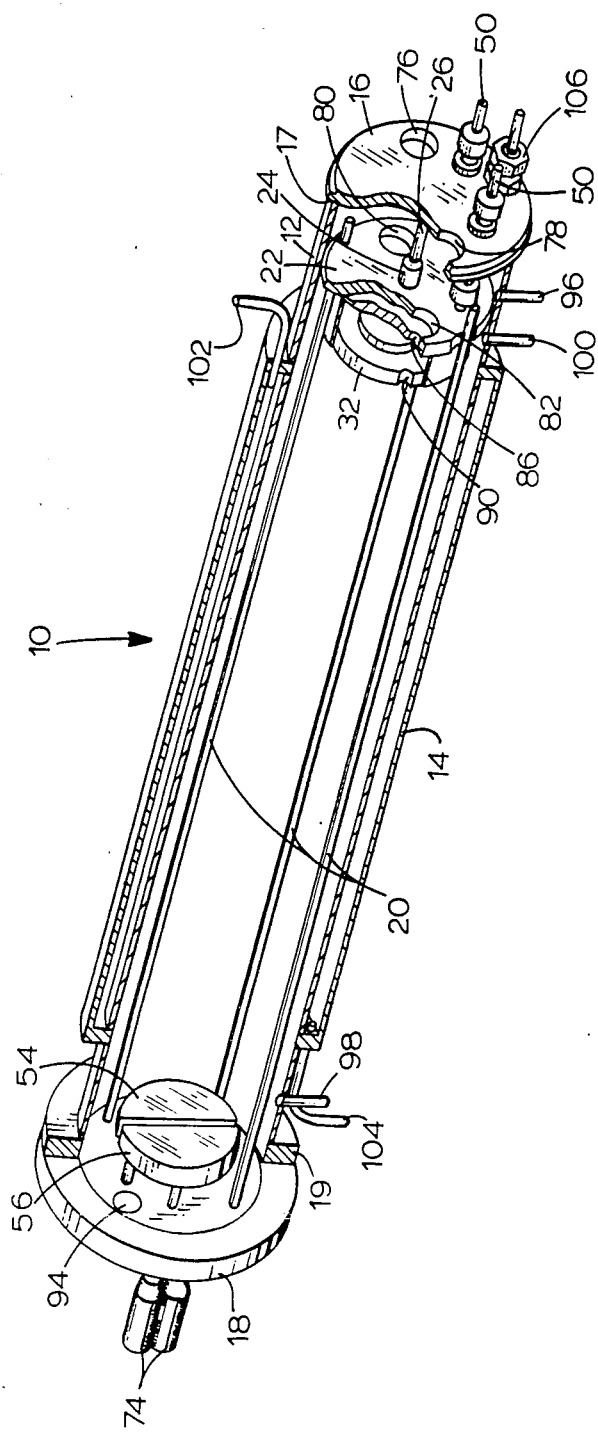
FIG. 1 is a perspective view of applicants' absorption cell in partial cross section.
Figure 2:
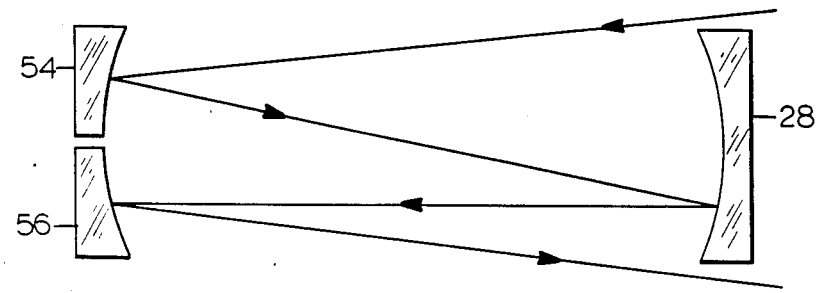
FIG. 2 is a schematic view of the mirror placement and optical path.
Figure 3:
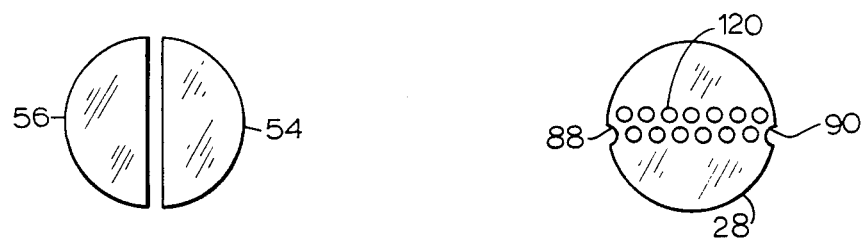
FIG. 3 is a schematic view of the mirrors and images on the Tee mirror.
Figure 5:
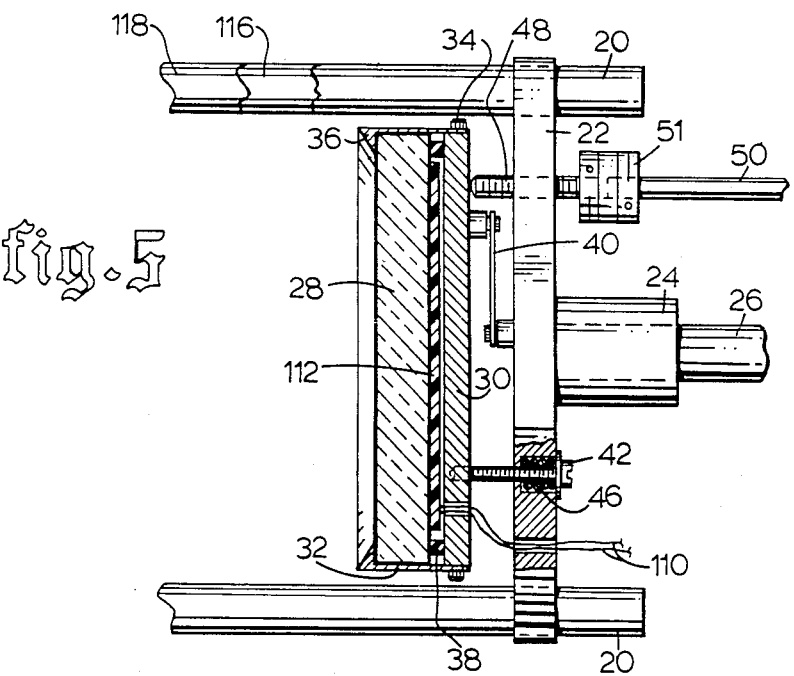
FIG. 5 is a detail of the Tee mirror support and adjustment mechanism in cross section.

Referring in more detail to the drawings, FIG. 1 shows a White-type absorption cell 10 having a stainless steel tubular body 12 surrounded by a temperature control jacket 14. The body of the cell 12 is closed by front end flanges 16, 17 and back end flanges 18, 19, as shown. The flanges can be joined in a conventional manner, e.g., clamp rings or bolts, not shown. A set of support rods 20 are threaded into back flange 18, in the interior of body 12, as shown. Rods 20 extend from back flange 18 in a cantilever fashion and support a mirror support plate 22, shown at the right in FIG. 1. Mirror support plate 22 can be fixed to rods 20 in a manner so that it may be adjusted as a rough mirror focusing adjustment, e.g., by a clamping arrangement, friction fit or screws, not shown. Mirror support plate 22 has a support socket 24 on the right side thereof, as shown in FIGS. 1 and 5, which receives a support post 26 therein. Support post 26 is threaded into front end flange 16 in the interior of cell 10, as shown in FIG. 4. Support post 26 is slidably engaged in the interior of support socket 24 to permit relative lateral movement between support socket 24 and support post 26.

As can be seen with more clarity in FIG. 5, Tee mirror 28 is mounted to mirror support plate 22 by a mirror backing plate 30. Mirror 28 is joined to mirror backing plate 30 by two semi-circular mirror retaining rings 32 which surround mirror 28 and are fastened to the periphery of mirror backing plate 30 by bolts 34, as shown in FIG. 5. Lip portions 36 at the extremity of retaining rings 32 hold mirror 28 in place against O-ring cushion 38 placed between mirror 28 and mirror backing plate 30. Mirror backing plate 30 is attached to mirror support plate 22 by two symmetrically mounted leaf springs 40 connected between mirror backing plate 30 and mirror support plate 22, one spring 40 is shown in FIG. 5. In addition, the suspension of mirror 28 and mirror backing plate 30 includes three adjusting screws and two spring loaded retaining screws. Retaining screws 42 pass through mirror support plate 22 and are threaded into backing plate 30, as shown. Retaining screws 42 have tensioning springs 46 to hold mirror backing plate 30 against the adjustment screws 48 in the position in which it is set. The suspension assembly also includes three orthogonally placed adjustment screws 48, as shown in schematic in FIG. 7. Adjusting screws 48 are threaded through support plate 22 and preferably have a fine pitch, so that small adjustments in the position of mirror 28 may be made. Adjusting screws 48 may be manipulated from outside of cell 10 by adjustment rods 50 which are connected by flexible couplings 51. Adjustment rods 50 pass through pressure tight slip fittings 52 in flange 16, as shown. Slip fittings 52 may be Teflon (TM) lined, not shown.

Referring to the left end of the cell 10, as shown in FIGS. 1 and 4, a set of Dee mirrors 54 and 56 are mounted on flange 18, as described herein. Peripheral retaining rings 58 and 60 hold mirrors 54 and 56 on mirror backing plates 62 and 64, as previously described for retaining rings 32. O-ring cushions 66 and 68 are positioned between mirrors 54 and 56 and mirror support plates 62 and 64. Dee mirrors 54 and 56 are each suspended from flange 18 by a series of three flexure rods, as shown in schematic in FIG. 6. The flexure rods are placed to provide tilt and alignment adjustments to Dee mirrors 54 and 56, as described herein. Flexure rods 70 are fixed to flange 18, as shown in FIG. 4, and are fixed to support plates 62 and 64, respectively, for Dee mirrors 54 and 56, for example, by screw threads. Flexure rods 72 are also fastened to mirror support plates 62 and 64, for example by screw threads, as shown in FIG. 4, and pass through pressure tight slip fittings 73 in flange 18, as shown. Slip fitting 73 may have O-ring seals. Flexure rods 72 are engaged by micrometer adjusters 74, mounted on flange 18, as shown. Micrometer adjusters 74 may have tensioning springs 75, as shown, to retain the setting of the mirror adjustment. Micrometer adjusters 74 extend or retract rods 72, as needed, to provide adjustment to Dee mirrors 54 and 56.

Cell 10 is provided with apertures 76 and 78 in flange 16 and with corresponding apertures 80 and 82 in mirror support plate 22. Mirror backing plate 30 also has corresponding apertures 84 and 86 and Tee mirror 28 has corresponding apertures 88 and 90, as shown, at the periphery of mirror 28. Apertures 76, 80, 84 and 88 are aligned, as are apertures 78, 82, 86 and 90. Apertures 76 and 78 have windows, such as window 92 shown in FIG. 4, which may be mounted in a manner known in the art. The windows i.e., window 92, may be glass, quartz or other material transparent to light of the wavelength which is being examined in cell 10. Flange 18 is also provided with aperture 94 which may also be provided with a window, not shown, of the type described for window 92.

Cell 10 is provided with an inlet 96 and an outlet 98 through which gas may be circulated through the cell 10 to purge the cell or to introduce and mix a sample or samples for examination. The cell 10 has an auxiliary connection 100 which may be connected to a vacuum source to evacuate cell 10 and to maintain a low pressure in cell 10 during use. Cell 10 is also provided with a heating jacket 14 having an inlet 102 and an outlet 104, as shown, through which a heating or cooling medium from a remote source may be circulated. Heating jacket 14 permits the temperature of cell 10 to be maintained at a chosen temperature for a particular experiment run. Flange 16 has an access fitting 106 through which connections 107 for thermocouples 108 are passed into the interior of cell 10. Electrical service connections 110 also pass through fitting 106 into the interior of cell 10. Electrical service 110 is connected to heating elements 112, as shown in FIG. 5, on the back of mirrors 28, 54 and 56. Heating elements 112 are conventional wire resistance heating elements bonded between two sheets of polymer film, such as Kapton (TM). The film is bonded to the back of the mirrors 28, 54 and 56 by a low vapor pressure adhesive, not shown. Heating elements 112 maintain the mirrors at a chosen temperature, preferably one or two degrees above the condensation point of any condensable material in the gas which is examined.

The body 12 and flanges 16, 17, 18 and 19 of cell 10 are preferably made of a material, such as stainless steel, to provide a corrosive resistant structure. The corrosion resistant properties of cell 10 may be increased by coating the interior with a corrosion resistant material, such as Teflon (TM) polytetrafluoroethylene, shown at 114 in FIG. 4. The internal components of cell 10, such as mirror support plate 22, mirror backing plates 30, 62 and 64, the adjusting screws 42, 48, the adjusting rods 70 and 72, and especially support rods 20, may be formed of Invar (TM) or some equivalent material having an extremely low coefficient of thermal expansion, so that the spacing between the mirrors 28, 54 and 56 remains substantially constant and thus the optical path transversed by light in the cell 10 remains substantially constant. Invar is described in *Marks' Standard Handbook for Mechanical Engineers,* 8th Ed., Baumeister et al, pp. 6–41. The Invar components are preferably plated with a corrosion resistant film or films such as a plated layer of nickel 116 over which has been plated a layer of chromium 118. To minimize reflections inside cell 10 the chromium plating is left in a dull flat form. It is not buffed out to a polished surface.

As will be appreciated from the drawings and the description given herein, the dimensional stability of applicants' White-type cell is maintained over a wide range of temperatures and operating conditions by applicants' unique cantilevered mounting structure. All stabilized structural components originate on flange 18, as the reference plane. The body 12 of cell 10 is free to expand and contract under the influence of the working conditions of the cell, i.e. temperature and pressure, but the mirror spacing remains substantially constant. The Invar support structure (rods 20) and the working mechanism is cantilevered from flange 18 and extends through the interior of cell 10. Support socket 24, at the right in FIG. 4, is supported vertically by support rod 26. Support rod 26 slides in socket 24 and is free to move subject to the expansion and contraction of body 12 of cell 10 without transmitting the expansion or contraction to the rods 20 forming the mounting structure. Similarly, mirror adjustments 50 join with flexible couplings 51 which do not transmit the expansion and contraction of body 12 to the mirror mounting and support mechanism, 22, 30. Mirror adjustment 72 may also be joined with a flexible coupling such as a bellows, not shown, if desired. Flange 16 is free to move without transmitting movement to the mirrors 28, 54, 56. Flange 18 remains the reference plane for the mirror support mechanism.

Applicants' cell 10 permits much more flexibility in the conditions for examination of gas specimens, such as condensable gases. The cell 10 can be operated both below and above normal atmospheric pressure and at a variety of temperatures, for example, from −10 degrees C. to 80 degrees C. Heating jacket 14 permits cell 10 to be operated at elevated temperatures, to prevent condensation, and mirror heaters 112 prevent the condensation of gases on the mirror surfaces themselves. In this regard applicants' have found that it is helpful if the heating fluid line 102 is plumbed in parallel with the gas entry line 96 and co-insulated. This serves to pre-heat the gas sample prior to its introduction into cell 10 and further reduces the possibility of condensation. It will be appreciated that the heat exchange jacket 14 can utilize a variety of thermal fluids, such as ethylene glycol, thermal oils and the like, which can be heated or cooled by a remote source, such as an immersion heater provided with a pump, as is known in the art. The entire cell can be insulated, for example, by conventional foam insulation, not shown, to aid in temperature control.

It will be appreciated that this cell 10 can be used for all purposes for which conventional White-type cells are used. Cell 10 can be used with a conventional spectrophotometer to measure the spectra and intensity of light passing through a gas sample. This configuration permits determination of the composition of an unknown gas sample. Cell 10 can also be used to determine the light absorption of a gas sample of known composition, using the equation previously described.

Applicants' cell allows both the pressure and the optical path length to be increased in a small cell. For example, using white light and a cell of nominal one meter length, eighty or more traversals can be obtained by applicants' cell. The traversals can be determined by checking the images 120 on Tee mirror 28, in the manner known in the art. Aperture 94 permits images 120 to be observed visually. The light from a source, not shown, enters applicants' cell 10 through aperture 76 and passes through apertures 80, 84 and 88 to Dee mirror 54. Light from Dee mirror 54 is focused on Tee mirror 28 which reflects it to Dee mirror 56. Light from Dee mirror 56 may be refocused on Tee mirror 28 for multiple path traversals or on exit aperture 90. The light will ultimately exit through apertures 90, 86, 82 and 78 to be examined, for example by a spectrophotometer. The aiming and orientation of Dee mirrors 54 and 56 is controlled by the operation of micrometer adjusters 74 and rods 72. Mirrors 28, 54 and 56 are concave mirrors having the same radius of curvature, as is known in the art.

As can be seen, the entire inner assembly is readily removable from cell 10 by disconnecting flanges 18 and 19 and sliding the assembly through the open end of cell 10, at the left in FIG. 4. Once removed, the Tee mirror 28 can be set or the entire assembly quickly replaced and reconnected. Coarse adjustments to Tee mirror 28 position, for focusing of the optical system can be made by a manipulation of support 22 on rods 20. Fine adjustment of focus and orientation can be made from the exterior of cell 10 by manipulation of screws 48 by rods 50. Likewise Dee mirrors 54 and 56 can be angularly adjusted by operation of micrometer adjusters 74 through rods 72. This adjustment also is made from the exterior of cell 10.

It will be understood that various changes can be made in the details, materials and arrangements, parts and operating conditions which have been described and illustrated with relation to the preferred embodiment. The above description is given to explain the nature of the invention to those skilled in the art. The invention is not to be limited to the details of the preferred embodiment, but only by the scope of the claims appended hereto and the equivalents thereof.

We claim:

1. A light absorption cell having a light path of the White-type wherein the improvement comprises means stabilizing the length of the light path against expansion and contraction of the cell over a wide range of operating temperatures, the cell having an enclosure for maintaining a working environment and the light path including a frame having mirrors mounted thereon defining the light path, the stabilizing means including means isolating the frame from expansion and contraction of the cell enclosure to prevent transmission of expansion and contraction from the enclosure thereto; the frame being formed of a material having a low coefficient of thermal expansion to further stabilize the optical system against expansion and contraction over a wide range of operating temperatures.

2. The device of the claim 1 wherein the cell has means to adjust and control the light path from the exterior of the cell.

3. The device of claim 1 wherein the cell has means to operate at pressures above and below atmospheric.

4. The device of claim 1 wherein the cell has means to control the temperature of the cell.

5. The device of claim 1 wherein the cell has access means for temperature controls.

6. The device of claim 1 wherein the light path includes mirrors and the mirrors have heaters to prevent condensation.

7. The device of claim 1 wherein the cell has a heating and cooling jacket.

8. The device of claim 7 wherein the cell has temperature sensing means to control the ambient temperature of the cell.

9. A light absorption cell having a light path of the White-type including means stabilizing the length of the light path against expansion and contraction of the cell over a wide range of operating temperatures, the light path including mirrors and the mirrors including means for preventing condensation thereon including heaters, and wherein the heaters are resistance heaters laminated in a thin polymer film and wherein the heaters are bonded to the backs of the mirrors by a low vapor pressure adhesive, the heaters applying heat directly to the mirrors and being effective to prevent condensation of condensable gases on the mirrors including being effective to prevent condensation of condensable gases on the mirrors under elevated pressures and at reduced temperatures.

10. A light absorption cell having a light path of the White-type wherein the improvement comprises means stabilizing the length of the light path against expansion and contraction of the cell over a wide range of operating temperatures, the cell including an enclosure and a frame located in the enclosure, the frame having mirrors mounted thereon forming an optical system defining the light path, the frame being cantilever mounted on a first end of the enclosure and extending from the first end of the enclosure to a location remote therefrom, the frame being formed of a material having a low coefficient of thermal expansion to stabilize the optical system against expansion and contraction over a wide range of operating temperatures.

11. The device of claim 10 wherein the frame is made of Invar.

12. The device of claim 11 wherein the frame is coated by plating to prevent corrosion thereof and wherein the coating is non-reflective.

13. The device of claim 10 wherein the cell has a mirror support plate mounted on the frame, the mirror support plate being attached to the frame, the cell having a mirror mounting plate therein connected to the mirror support plate, the connection including means for adjusting the mirror mounting plate.

14. The device of claim 13 wherein the mirror mounting plate includes a mirror retaining means and a mirror mounted therein.

15. The device of claim 13 wherein the cell has mirror heating means mounted to the mirror.

16. The device of claim 10 wherein the enclosure is Teflon lined.

17. The device of claim 10 wherein the mirrors include a Tee mirror and a set of Dee mirrors, the mirrors being mounted on plates, the plates for the Dee mirrors being mounted to the enclosure at an end thereof and the plate for the Tee mirror being mounted to the frame at a location remote from the end of the enclosure, the mirrors defining an optical path therebetween.

18. A white-type light absorption cell having an enclosure, the enclosure being substantially closed, the enclosure having a first end, the cell having a mirror mounting frame in the enclosure, the mirror mounting frame including a plurality of rods connected to the enclosure at the first end and extending into the enclosure, the enclosure having a second end and the rods extending to a location adjacent to the second end but spaced therefrom, the cell having two first mirrors mounted in the enclosure at a location adjacent to the first end, the first mirrors each having a first mirror mounting plate, the first mirror mounting plates being connected to the first end of the enclosure and spaced therefrom, the connection including means to adjust the first mirror mounting plates, the cell having a second mirror support plate slidably mounted in the enclosure on the rods at a location adjacent to the second end, the cell having a second mirror mounting plate connected to the second mirror support plate, the connection including means to adjust the second mirror mounting plate, the cell having a second mirror mounted on the second mirror mounting plate and being adjustable therewith, the second mirror facing the first end, the first mirrors facing the second mirror and defining an optical path therewith, the adjusting means for the second mirror mounting plate and the first mirror mounting plates including means to adjust the second mirror mounting plate and the first mirror mounting plates from outside of the enclosure, the adjusting means including means to seal the enclosure, the second mirror mounting plate being connected to the second mirror support plate by resilient biasing means, the means to adjust the second mirror including a set of adjusting screws passing through the second mirror support plate and impinging on the second mirror mounting plate, the set of adjusting screws acting against the resilient biasing means to adjust the second mirror and the optical path, the means to adjust the first mirrors including sets of flexure rods connected to the first mirror mounting plates, at least one of the flexure rods in each set being operated from outside of the enclosure by an adjuster, the second mirror support plate having a socket mounted thereon and facing the second end of the enclosure, the second end of the enclosure having a support rod mounted thereon and extending into the enclosure, the support rod being slidably received in the socket and providing support to the second mirror support plate, the slidable fit between the socket and the support rod permitting the enclosure to expand and contract without transmitting the expansion or contraction to the second mirror support plate and the structure connected thereto, the second end of the enclosure having apertures and windows for introducing light into the cell and for removing light from the cell, the second mirror support plate, the second mirror mounting plate and the second mirror having apertures therein in register with the apertures in the second end of the enclosure permitting light entering the enclosure to impinge on a first mirror and permitting light from a first mirror to exit from the cell, the first end of the enclosure having an aperture and window permitting visual inspection of the interior of the cell, the mirrors having heating means to maintain the surfaces of the mirrors at a temperature above the condensation point of condensable gases, the cell having entrance and exit means for gas samples and having an auxilliary connection means, the cell having a jacket providing means for selectively heating and cooling the cell to regulate the ambient temperature therein, the cell having temperature sensor means to control the temperature of the cell at a preselected value.

19. A light absorption cell having a light path of the White-type wherein the improvement comprises means stabilizing the length of the light path against expansion and contraction of the cell over a wide range of operating temperatures, the cell having an enclosure and a frame located in the enclosure, the frame having mirrors mounted thereon forming an optical system defining the light path, the frame being formed of a material having a low coefficient of thermal expansion to stabilize the optical system against expansion and contraction over a wide range of operating temperatures, the frame being cantilever mounted on a first end of the enclosure and extending from the first end of the enclosure to a location remote therefrom, the frame having a socket mounted thereon at a location remote from the first end of the enclosure and adjacent to a second end of the enclosure and wherein the enclosure has a support rod mounted on the second end, one end of the support rod being slidably received in the socket and cooperating therewith to at least partially support the frame, the support rod and socket permitting relative movement there between to prevent the expansion and contraction of the enclosure from being transmitted to the frame.

* * * * *